(12) United States Patent
Fouroghalzaman

(10) Patent No.: US 11,073,490 B2
(45) Date of Patent: Jul. 27, 2021

(54) MEASURING DEVICE FOR BLOOD AND/OR LIQUID INTERSTITIAL ANALYTES

(71) Applicant: SENSOR HEALTH S.R.L., Trieste (IT)

(72) Inventor: Katouziantherani Moghadam Fouroghalzaman, Trieste (IT)

(73) Assignee: SENSOR HEALTH S.R.L., Trieste (IT)

( * ) Notice: Subject to any disclaimer, the term of this patent is extended or adjusted under 35 U.S.C. 154(b) by 46 days.

(21) Appl. No.: 15/769,531

(22) PCT Filed: Feb. 5, 2016

(86) PCT No.: PCT/IT2016/000030
§ 371 (c)(1),
(2) Date: Apr. 19, 2018

(87) PCT Pub. No.: WO2017/134692
PCT Pub. Date: Aug. 10, 2017

(65) Prior Publication Data
US 2018/0340902 A1    Nov. 29, 2018

(51) Int. Cl.
  *G01N 27/00*  (2006.01)
  *A61B 5/00*   (2006.01)
  *G01N 27/06*  (2006.01)
  *A61B 5/145*  (2006.01)

(52) U.S. Cl.
  CPC .......... *G01N 27/06* (2013.01); *A61B 5/14532* (2013.01); *A61B 5/14546* (2013.01); *A61B 5/688* (2013.01); *A61B 5/6844* (2013.01); *A61B 2560/0443* (2013.01)

(58) Field of Classification Search
  CPC ............ A61B 5/14546; A61B 5/14532; A61B 5/1451; A61B 5/688
  See application file for complete search history.

(56) References Cited

U.S. PATENT DOCUMENTS

| | | | |
|---|---|---|---|
| 2004/0015063 A1 * | 1/2004 | DeNuzzio | A61B 5/14532 600/347 |
| 2005/0096519 A1 | 5/2005 | DeNuzzio et al. | |
| 2007/0027384 A1 | 2/2007 | Brister et al. | |
| 2019/0022385 A1 * | 1/2019 | Hadvary | A61B 5/4839 |

FOREIGN PATENT DOCUMENTS

JP    2007000517 A    1/2007

* cited by examiner

*Primary Examiner* — Christopher Adam Hixson
(74) *Attorney, Agent, or Firm* — Pearne & Gordon LLP

(57) ABSTRACT

A device for measuring analytes in the blood and/or in the interstitial fluid, comprising: at least one sensor (2) configured to be in contact with the blood and/or interstitial fluid; a transducer (15) engaged to said sensor (2) to measure the concentration of said analyte in the blood and/or interstitial fluid; electronic processing means (16) associated to the transducer (15) to generate a signal (S) representative of the concentration value of said analyte in the blood and/or interstitial fluid; and transmitting means (17) associated with the electronic processing means (16) to send the signal to a receiver member (17a) remotely arranged with respect to said electronic processing means (16); said sensor (2) comprising an active electrode (3) having at least a needle (4) insertable into the skin to be in contact with the blood and/or interstitial fluid, and a reference electrode (5) having a contact element (6) with the user's skin; said electrodes (3, 5) defining a respective current passage electrical circuit.

12 Claims, 5 Drawing Sheets

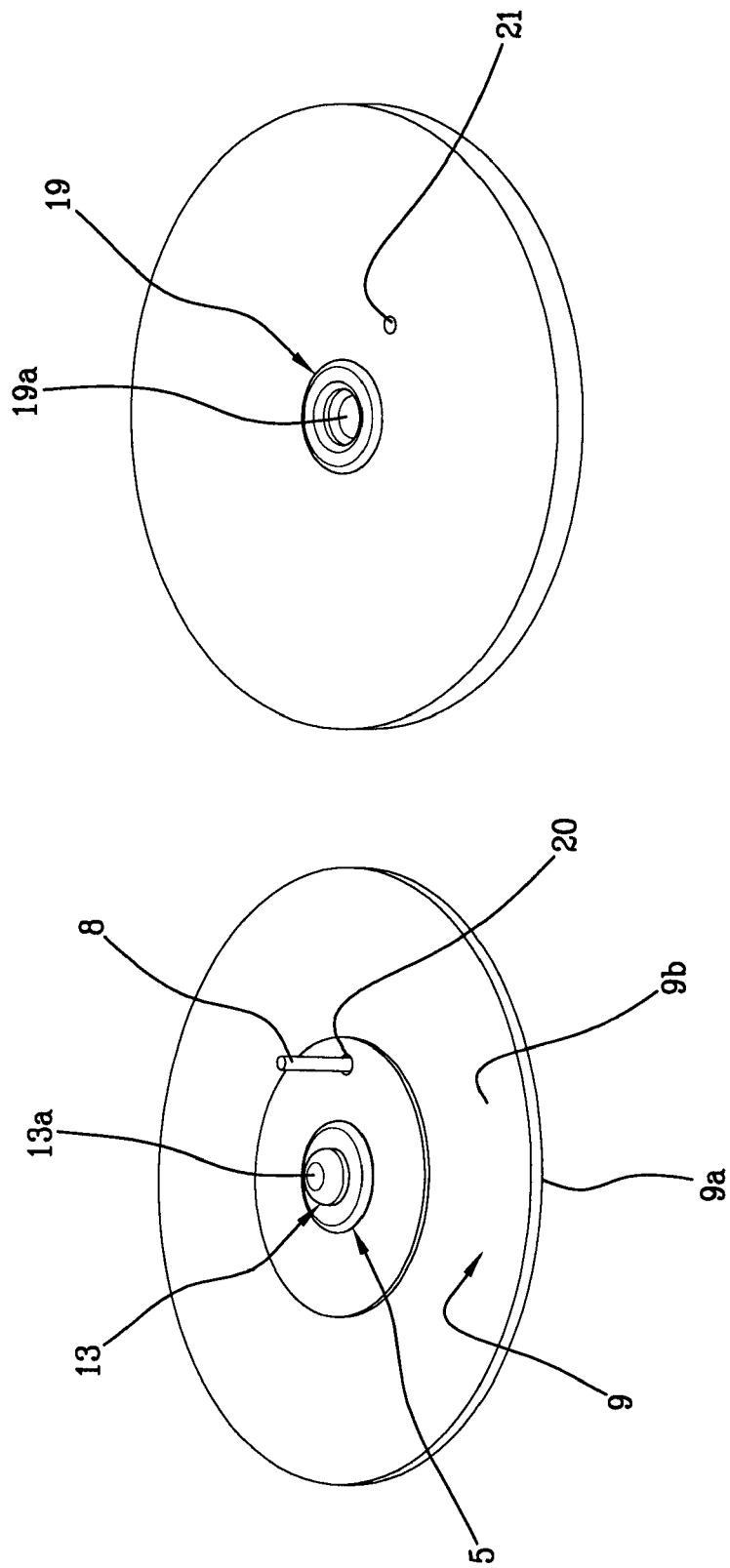

MEASURING DEVICE FOR BLOOD AND/OR LIQUID INTERSTITIAL ANALYTES

TECHNICAL FIELD

The present invention relates to a device for measuring analytes in the blood and/or in the interstitial fluid.

In particular, the present invention relates to a device for detecting and measuring the level of an analyte, such as glucose, in the blood and/or in the interstitial fluid. The device is applied to a user to constantly monitor the analyte (glucose) concentration contained in the body fluid and, thus, to provide a parameter representative of the user's health status.

STATE OF THE ART

It is known that devices for detection and monitoring of analytes in the human body generally consist of biosensors applied to the body to come into contact with the body fluid. The biosensors are operatively associated with transducers, generally of the electrochemical type, able to react with a predetermined analyte, such as glucose.

For example, in the specific case of devices used by people suffering from diabetes, suitable for the measurement of glucose level in the blood, blood-contacting devices are able to provide the glucose level in a short time. Such data is sent to an electronic display support to inform the user about his/her health status.

For this purpose, devices which provide for the use of a needle which is manually inserted into the user's skin (generally the finger is punctured) to come into contact with the blood are known. Although such a device can give the user a precise indication, it has some practical drawbacks, mainly related to skin laceration actions, necessary to contact the biosensor with the blood.

To overcome this drawback, a device having an adhesive support (patch) provided with a needle protruding from the adhesive surface of the support itself has been developed.

The support also has a transducer and a related processing logic and data transmission unit.

Such device is maintained in contact with the skin by means of the adhesive surface, also allowing the constantly maintenance of the needle inside the body.

Thus, the glucose level analysis is automatically performed by the electronic processing unit analysing blood glucose level through the needle permanently inserted into the skin. Monitoring is done at predetermined intervals to send a set of signals related to the glucose level. Such signals are displayed by the user through appropriate electronic equipment provided with a monitor, to possibly provide for insulin administration.

After a predetermined usage period of the adhesive support, the same is removed from skin and replaced in order to ensure proper skin adhesion characteristics and, in general, to ensure proper device integrity which, inevitably, tends to be damaged due to a prolonged usage.

However, such devices, although able to avoid the actions of continuous user's skin laceration to determine the contact between the blood and the biosensor, have important drawbacks.

First, it should be noted that the device application briefly described above is particularly complex due to the necessity to correctly arrange the needle so that it may be in contact with the blood. Therefore, an incorrect application of the entire device determines the incorrect or impossible reading of the glucose level.

Furthermore, due to the required size of the needle that effectively constitutes the biosensor, its skin penetration is particularly painful, and, therefore, not applicable to subjects particularly sensitive to pain such as children.

It should also be noted that, as a result of accidental tampering derived from involuntary impacts, the adhesive support may move or detach, thus compromising the correct operation. Also the electronic sensor part, arranged externally with respect to the adhesive surface and, thus, more exposed to potential impacts, bumps or accidental impacts, appears to be damageable, with consequent replacement of the entire system.

Finally, it should be noted that the device described above is structurally complicated, thus has high costs, especially for the presence of electronic components. In this regard, the periodic replacement of the device, necessary to ensure the correct operation or to allow the user to dip in water or play sports without damaging the electronic components, determines a huge increase in the usage costs of such a device.

OBJECT OF THE INVENTION

In this context, the technical task underlying the present invention is to propose a device for measuring analytes in the blood and/or in the interstitial fluid that overcomes the drawbacks of the above-mentioned prior art.

In particular, it is an object of the present invention to provide a device for measuring analytes in the blood and/or in the interstitial fluid, in particular for glucose measuring, which is structurally simple and low-cost.

In greater detail, it is an object of the present invention to provide a device for measuring analytes in the blood and/or in the interstitial fluid, which is reliable and which may be applied in a simple and safe way by the user, always ensuring the correct measurement of the analyte concentration.

Again, it is an object of the present invention to propose a device for measuring analytes in the blood and/or in the interstitial fluid, which is applicable by anyone because it cannot cause pain during its application.

Finally, it is an object of the present invention to propose a device for measuring analytes in the blood and/or in the interstitial fluid which is also usable in water or during sports without causing damage to internal components of the device itself.

The mentioned technical task and the specified objects are substantially achieved by a device for measuring analytes in the blood and/or in the interstitial fluid, comprising the technical characteristics set out in one or more of the appended claims.

Particularly, the present invention provides a device for measuring analytes in the blood and/or in the interstitial fluid, comprising: at least one sensor configured to be in contact with the blood and/or interstitial fluid; a transducer engaged to said sensor to measure the concentration of said analyte in the blood and/or interstitial fluid; electronic processing means associated with the transducer to generate a signal representative of the concentration value of said analyte in the blood and/or interstitial fluid; and transmitting means associated with the electronic processing means to send the signal to a receiver member arranged remotely with respect to said electronic processing means. The sensor comprises an active electrode having at least a needle insertable into the skin to be in contact with the blood and/or interstitial fluid, and a reference electrode having a contact element with the user's skin; said electrodes defining a respective current passage electrical circuit.

BRIEF DESCRIPTION OF THE DRAWINGS

Further features and advantages of the present invention will become more apparent from the indicative description, and therefore not limited to a preferred but not exclusive embodiment of a device for measuring analytes in the blood and/or in the interstitial fluid, as illustrated in the appended drawings, in which:

FIG. 4 shows a perspective view of two components of the device of FIG. 1, uncoupled from one another;

DETAILED DESCRIPTION OF PREFERRED EMBODIMENTS OF THE INVENTION

Figures 1, 2:
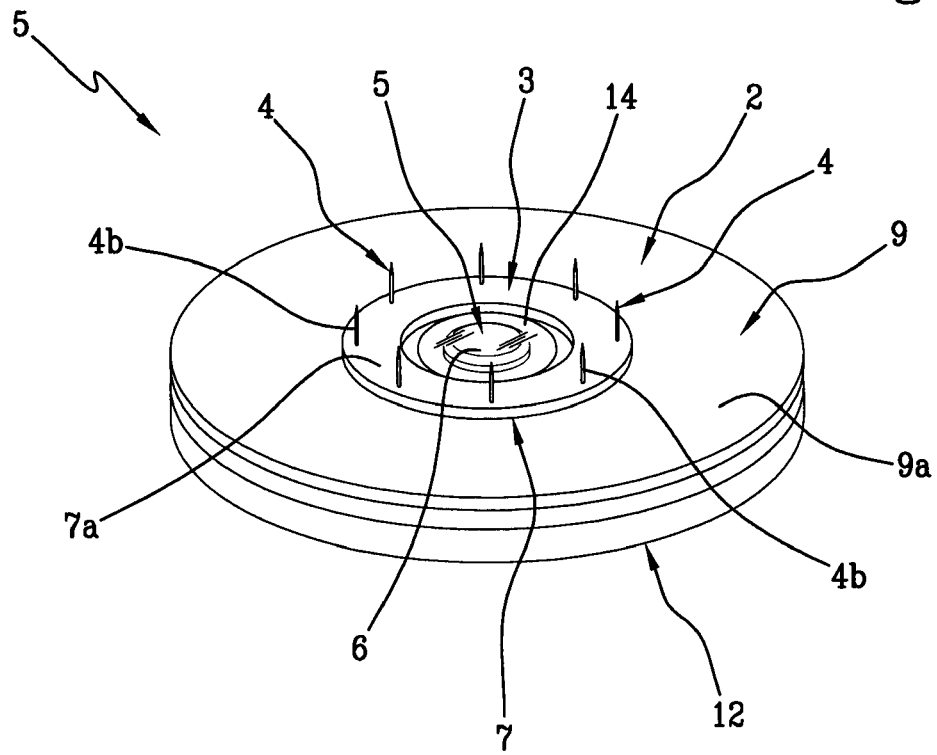
FIG. 1 is a perspective view of the device for measuring analytes in the blood and/or in the interstitial fluid according to the present invention.
FIG. 2 is a sectional side elevational view of the device of FIG. 1.
Figure 3:
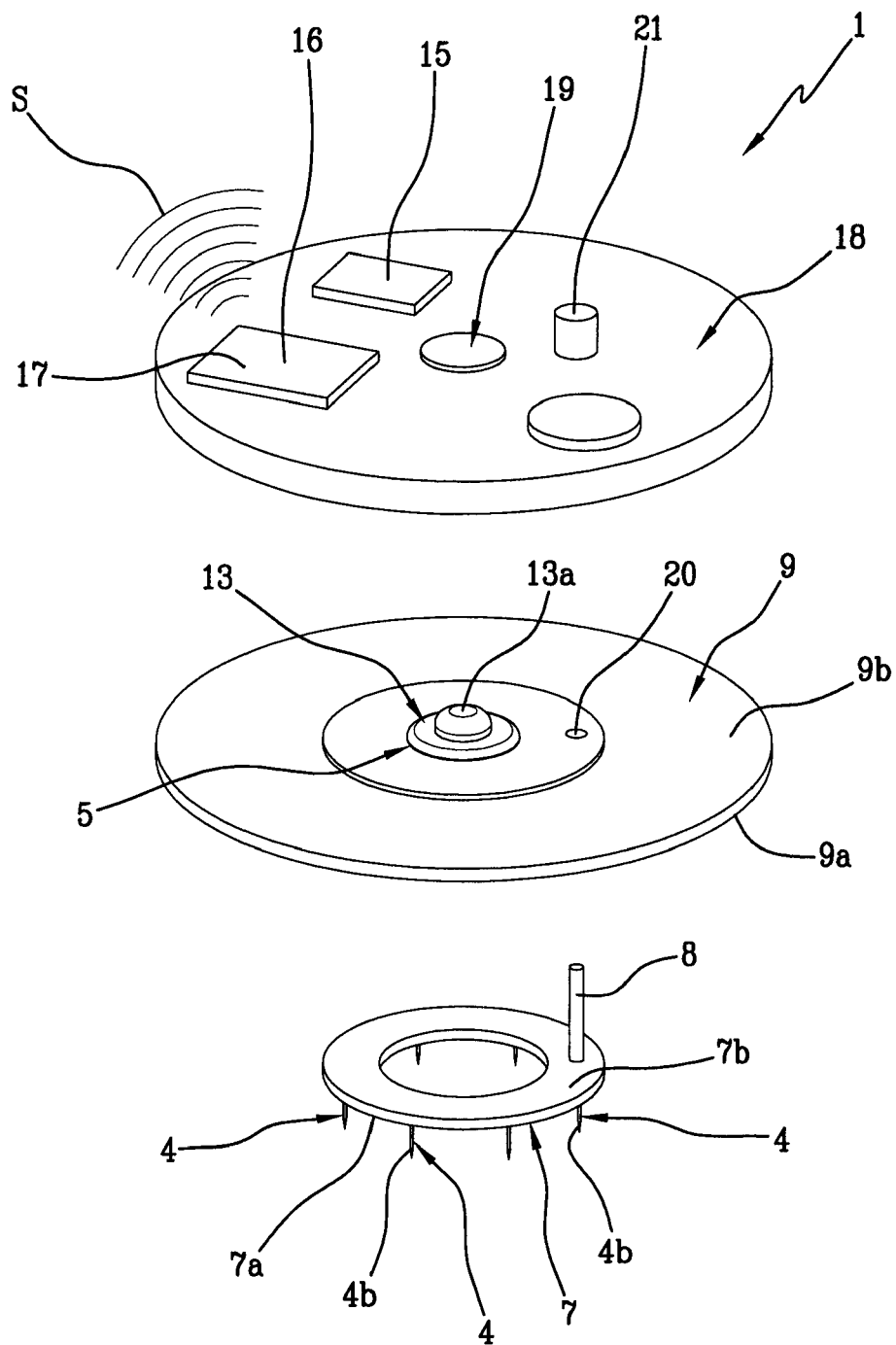
FIG. 3 is an exploded perspective view of the device of FIG. 1.

With reference to the attached figures, the number 1 globally indicates a device for measuring analytes in the blood and/or in the interstitial fluid according to the present invention.

Particularly, the present invention finds application for glucose measuring in the body fluid. However, it should be specified that the present invention may be employed for measuring cardiac biomarkers, tumour biomarkers, or any other analytes in the body fluid.

In greater detail, the device 1 comprises at least one sensor 2, configured to be in contact with the blood and/or interstitial fluid.

Advantageously, the sensor 2 has an active electrode 3 having at least a needle 4 insertable into the user "U" skin to be in contact with the blood and/or the interstitial fluid.

Sensor 2 has also a reference electrode 5 having a contact element 6 with the user "U" skin.

As will be better clarified in the following discussion, the electrodes 3 and 5 define a respective current passage electrical circuit.

The active electrode 3 preferably includes a plurality of needles 4, arranged alongside each other and arranged along a substantially circular path.

Each needle has a diameter between 0.1 mm and 0.19 mm and a length between 500 µm and 3 mm.

Preferably, a number of needles 4 which may be comprised between 1 and forty is provided. Advantageously, the number of needles 4 is comprised in a range between six and eight. Furthermore, each needle 4 has advantageously a diameter equal to 0.14 mm and a length equal to 3 mm.

Each needle 4 comprises a bioreceptor able to react with the respective analyte. Such bioreceptor may be defined by an enzyme, antibody, DNA/RNA according to the type of analyte to be measured.

In accordance with a first embodiment illustrated in FIGS. 1 to 4, the active electrode 3 further comprises a carrier body 7 of the needles 4 having an annular configuration and defining a first contact surface 7a with the user "U" skin and a second surface 7b (FIG. 3) opposite to the first surface 7a. In this condition, it should be noted that the needles 4 are mutually arranged alongside and protruding from the first surface 7a of the carrier body 7. The needles 4 have an engaging end 4a engaging the carrier body and a free end 4b to be inserted into the user "U" skin.

The engaging ends 4a of the needles 4 are in mutual electrical contact (not shown in the appended figures) with a respective connector 8 substantially having a pin configuration and protruding from the second surface 7b of the carrier body 7.

Furthermore, the device 1 comprises a support element 9 of the reference electrode 5 having an adhesive surface 9a engageable to the user "U" skin and an outer surface 9b opposite to the adhesive surface 9a.

The carrier body 7 is engaged to the support element 9 with the respective second surface 7b stably associated with an annular zone of the adhesive surface 9a. In detail, with particular reference to FIG. 1, it should be noted that the support body 7 is associated in correspondence to said adhesive surface 9a in a location surrounding the reference electrode 5.

Figure 5A:
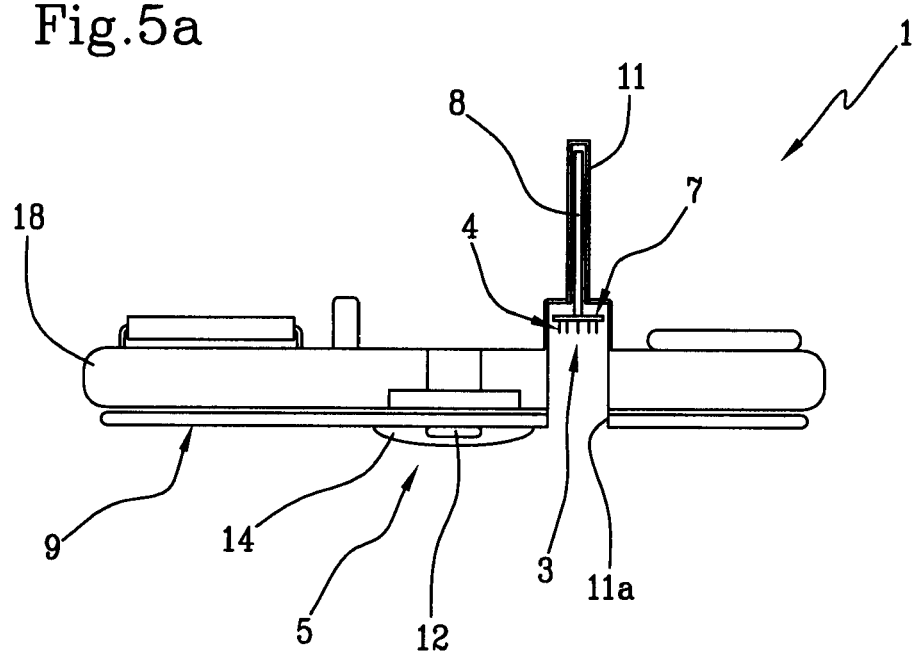
FIGS. 5a and 5b show sectional side elevational views of the device in accordance with a further embodiment and in respective operating conditions.
Figure 5B:
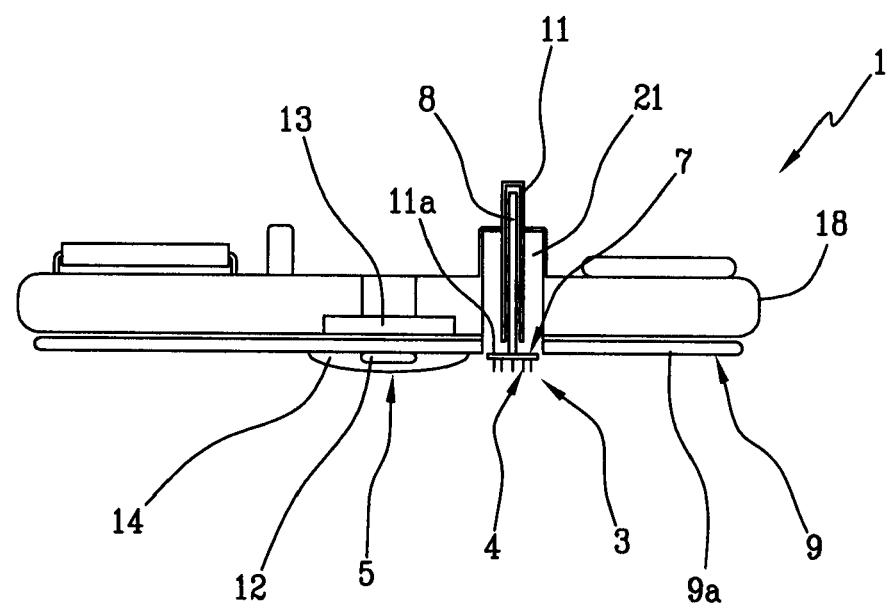
Figure 6:
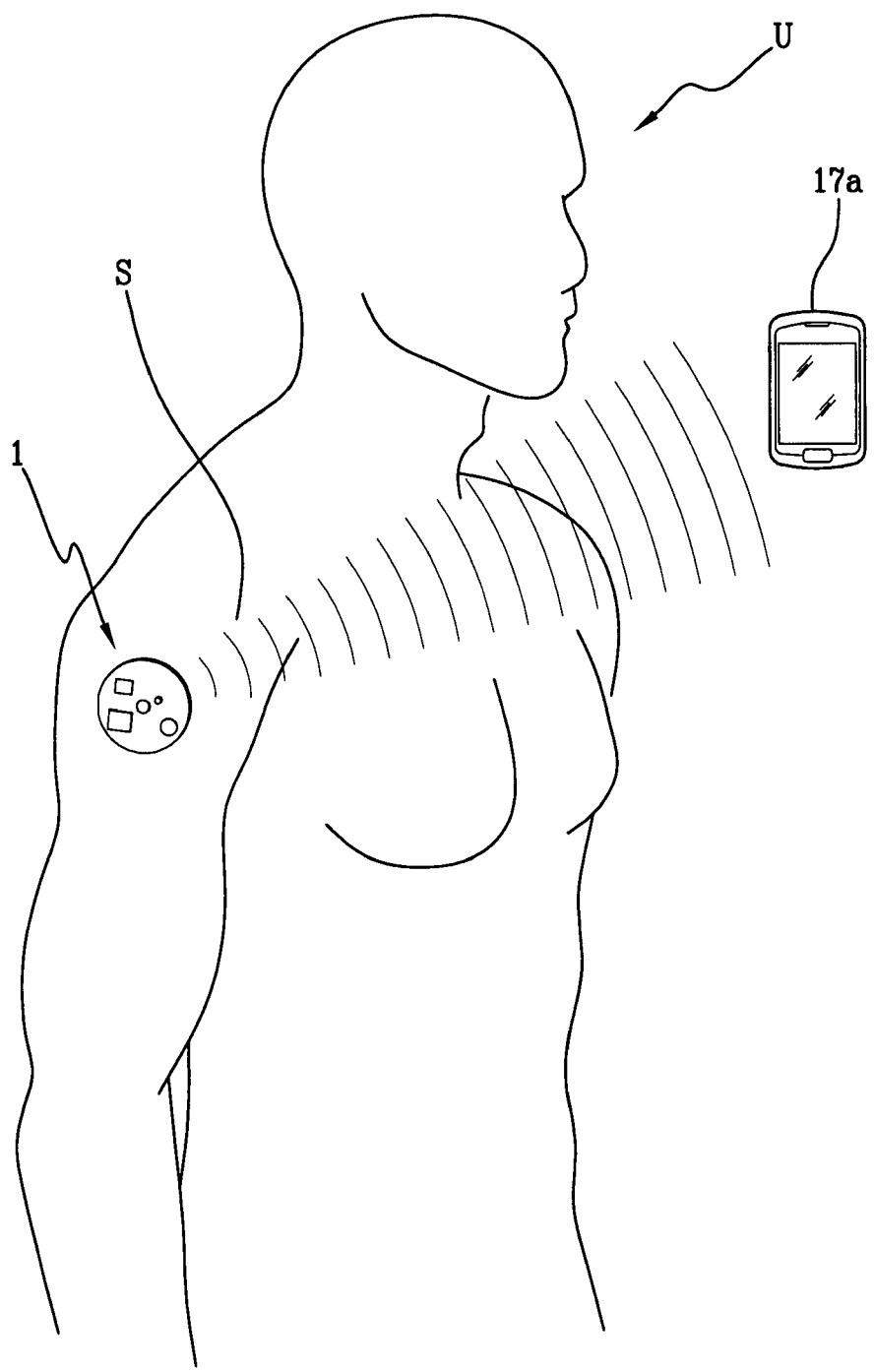
FIG. 6 shows a perspective view of the device in accordance with the present invention applied to a respective user.

In accordance with the second embodiment illustrated in FIGS. 5a and 5b, the active electrode 3 has a carrier body 7, substantially having a disk configuration.

In this embodiment solution, the carrier body 7 is movable in a respective housing seat 10 between a non-operating condition, in which the respective contact surface 7a is moved away from the skin and the free end 4b of the needles 4 is not inserted into the user "U" skin, and an operating condition, in which the contact surface 7a is abutted to the user "U" skin and the free end 4b of the needles 4 is inserted in said skin. The movement of the carrier body 7 is determined by an appropriate actuator 11, manually controllable by a pressing action to the user's skin.

It should be noted that, in the operating condition of the carrier body 7, the connector 8 closes the electrical circuit, whereas in the non-operating condition the connector 8 opens the electrical circuit stopping the electrical current passage.

It should also be noted that the carrier body 7 is positionable in the respective operating condition in a through opening 11a formed in the support element 9.

Advantageously, for both the embodiment solutions, the support element 9 is made of flexible fabric and has a circular configuration. Alternatively to the use of the fabric material, another material may be provided, which is sufficiently porous to ensure a good breathability in the skin area to which the device 1 is applied.

The reference electrode 5 is preferably arranged in the centre of the support element 9.

In particular, the reference electrode 5 includes an active portion 12 arranged in correspondence to the adhesive surface 9a and a connecting portion 13 arranged in correspondence to the outer surface 9b.

The active portion 12 has a surface coating 14 to promote the contact with the user's epidermis even in the presence of water and to allow the electrical connection between the electrodes 3, 5. Such surface coating 14 is composed of a gel material.

Furthermore, the device 1 comprises a known type transducer 15 and therefore not described and illustrated in detail, engaged to the sensor 2 for measuring the analyte concentration in the blood and/or interstitial fluid.

The transducer 15 may be of electrochemical (potentiometric, amperometric), photometric, colorimetric or optical type.

Furthermore, the transducer 15 is connected to electronic processing means 16 suitable to generate a signal "S" representative of the analyte concentration value in the blood and/or interstitial fluid. Furthermore, transmitting means 17 are provided associated with electronic processing means 16 in order to send the signal S to a receiver member 17a arranged remotely with respect to said electronic processing means 16. The receiver member 17a may be, for example, constituted by a smartphone or other similar device, having an appropriate display software of the analyte concentration value.

The transducer 15, the processing means 16 and the transmitting means 17 are arranged on a support base 18 constituted by a circular plate of the same dimensions of the support element 9. The base 18 has an electrical connecting element 19 (FIG. 4) to the reference electrode 5.

In particular, the connecting element 19 is removably engaged to the connecting portion 13 of the reference electrode 5 to define a mechanical coupling between the reference electrode 5 itself and the support base 19.

The connecting portion 13 of the reference electrode 5 preferably consists of a protrusion 13a insertable by mechanical interlocking within a seat 19a formed in the connecting element 19 to define a mechanical coupling and electrical contact condition. In order to release the base 18 from the support element 9 (and from the reference electrode 5), the protrusion 13a is extracted from the seat 19a to define a mechanical release condition.

As shown in FIG. 2, the connector 8 protruding from the second surface 7b of the carrier body 7 extends in a through hole 20 formed in the support element 9 to be insertable in a housing seat 21 formed in the base 18.

The housing seat 21 is provided in order to electrically contact the connector 8 with the transducer 15 and with said processing means 16 to define said circuit.

Similarly, also in the second embodiment solution of FIG. 5b, the connector 8 is in electrical contact with the electronic sensors.

Accordingly, through the connector 8 and through the mechanical coupling between the connecting portion 13 of the reference electrode 5 and the connecting element 19 of the base 18 said electrical circuit is defined, which connects together electrodes 2, 5 with the electronic components composed of the transducer 15, the processing means 16 and the transmitting means 17.

Advantageously, the detection carried out by the sensor 2 connected to the transducer 15 allows the processing of a value generated by the processing means 16 as signal "S". Such signal "S" is consequently sent to the remote support in order to inform the user about the analyte concentration level.

The present invention has numerous advantages and achieves the intended aims.

In particular, the device 1 described above allows the measurement of analytes, such as glucose, in the blood and/or in the interstitial fluid.

Accordingly, the needle dimensions do not need to be too large to reach the blood placed under the epidermis.

Advantageously, a series of small-size needles are used, which do not cause pain sensations during application but, however, ensure the correct contact with the body fluid in which the analyte is.

Furthermore, the device 1 is structurally simple and low-cost, particularly thanks to the possibility of manually releasing the support base 18 of the electronic components from the electrodes 3, 5.

Furthermore, even after the removal and replacement of the entire device, it is possible to replace only the support element 9 of the electrodes 3, 5, thus, using the same electronic components.

The invention claimed is:

1. Device for measuring analytes in the blood and/or in the interstitial fluid, comprising:
   at least one sensor (2) configured to be in contact with blood and/or interstitial fluid;
   a transducer (15) engaged to said sensor (2) to measure the concentration of said analyte in the blood and/or interstitial fluid;
   an electronic processor (16) associated with the transducer (15) to generate a signal (S) representative of concentration value of said analyte in the blood and/or interstitial fluid; and
   a transmitter (17) associated with the electronic processor (16) to send the signal (S) to a receiver member (17a) remotely arranged with respect to said electronic processor (16);
   wherein said sensor (2) comprises an active electrode (3) having at least one needle (4) insertable into the skin to be in contact with the blood and/or interstitial fluid, and a reference electrode (5) having a contact element (6) with the user's skin; said electrodes (3, 5) defining a respective current passage electrical circuit; wherein said active electrode (3) comprises a plurality of needles (4) arranged alongside each other and arranged along a circular path, each needle (4) comprising a bioreceptor which is able to react with said analyte and having a diameter between 0.1 mm and 0.19 mm and a length between 500 µm and 3 mm; and wherein said active electrode (3) further comprises a carrier body (7) of said needles (4) having an annular configuration wherein the needles (4) are placed along the circular path, said annular carrier body (7) surrounding the reference electrode (5) and defining a first contact surface (7a) with the user's skin and a second surface (7b) opposite to the first (7a); said needles (4) being arranged around the reference electrode (5) and mutually arranged alongside, and protruding from said first surface (7a).

2. Device according to claim 1, characterized in that said active electrode (3) comprises between six and eight needles (4) and in that each needle (4) has a diameter equal to 0.14 mm and a length equal to 3 mm.

3. Device according to claim 1, characterized in that each needle (4) has an engaging end (4a) to said carrier body (7) and a free end (4b) of insertion into the user's skin; said engagement ends (4b) of the needles (4) being in mutual electrical contact with a respective connector (8) protruding from the second surface (7b) of the carrier body (7).

4. Device according to claim 1, characterized in that it further comprises a support element (9) of said reference electrode (5) having an adhesive surface (9a) engageable to the user's skin and an outer surface (9b) opposite to said adhesive surface (9a); said carrier body (7) being engaged to said support element (9) with the respective second surface (7b) stably engaged to an annular zone of said adhesive surface (9a) surrounding the reference electrode (5).

5. Device according to claim 1, characterized in that each needle (4) has an engaging end (4a) to said carrier body (7) and a free end (4b) to be inserted into the user's skin; said engagement ends (4a) of the needles (4) being in mutual electrical contact with a respective connector (8) protruding from the second surface (7b) of the carrier body (7).

6. Device according to claim 4, characterized in that said support element (9) is made from flexible fabric and has a circular configuration; said reference electrode (5) being disposed in the centre of the support element (9).

7. Device according to claim 4, characterized in that said reference electrode (5) comprises an active portion (12) arranged in correspondence to said adhesive surface (9a) and a connecting portion (13) disposed in correspondence to said outer surface (9b); said active portion (12) having a surface coating (14) to promote the contact with the user's epidermis and to allow the electrical connection between the electrodes (3, 5).

8. Device according to claim 7, characterized in that it further comprises a support base (18) of said electronic processor (16) and of said transducer (15), having an electrical connecting element (19) to said reference electrode (5).

9. Device according to claim 8, characterized in that said connecting element (19) is removably engaged to said connecting portion (13) of the reference electrode (5) to define a mechanical coupling between the reference electrode (5) coupled to the support element (9), and said support base (18).

10. Device according to claim 9, characterized in that said connecting portion (13) of the reference electrode (5) comprises a protrusion (13a) insertable by mechanical interlocking within a seat (19a) formed in said connecting element (19) to define a mechanical coupling and electrical contact condition; said protrusion (13a) being extractable from the seat (19a) formed in the connecting element (19) to define a mechanical release condition with said base (18) and electrical disconnection with said transducer (15) and processor (16).

11. Device according to claim 8, characterized in that said connector (8) protruding from the second surface (7b) of the carrier body (7) extends in a through hole (20) formed in the support element (9) to be insertable in a housing seat (21) formed in the base (18); said housing seat (21) electrically contacting the connector (8) with the transducer (15) and with said processor (16) to define said circuit.

12. Device for measuring analytes in the blood and/or in the interstitial fluid, comprising:
   at least one sensor (2) configured to be in contact with blood and/or interstitial fluid;
   a transducer (15) engaged to said sensor (2) to measure the concentration of said analyte in the blood and/or interstitial fluid;
   an electronic processor (16) associated with the transducer (15) to generate a signal (S) representative of concentration value of said analyte in the blood and/or interstitial fluid; and
   a transmitter (17) associated with the electronic processor (16) to send the signal (S) to a receiver member (17a) remotely arranged with respect to said electronic processor (16);
   said sensor (2) comprises an active electrode (3) having at least one needle (4) insertable into the skin to be in contact with the blood and/or interstitial fluid, and a reference electrode (5) having a contact element (6) with the user's skin; said electrodes (3, 5) defining a respective current passage electrical circuit;
   wherein said active electrode (3) comprises a plurality of needles (4) arranged alongside each other and arranged along a substantially circular path each needle (4) comprising a bioreceptor which is able to react with said analyte and having a diameter between 0.1 mm and 0.19 mm and a length between 500 µm and 3 mm;
   wherein said active electrode (3) further comprises a carrier body (7) of said needles (4) having an annular configuration wherein the needles (4) are placed along the circular path, said annular carrier body (7) surrounding the reference electrode (5) and defining a first contact surface (7a) with the user's skin and a second surface (7b) opposite to the first (7a); said needles (4) being arranged around the reference electrode (5) and mutually arranged alongside, and protruding from said first surface (7a);
   wherein it further comprises a support element (9) of said reference electrode (5) having an adhesive surface (9a) engageable to the user's skin and an outer surface (9b) opposite to said adhesive surface (9a); said support element (9) being made from flexible fabric and having a circular configuration; said reference electrode (5) being disposed in the centre of the support element (9); said carrier body (7) being engaged to said support element (9) with the respective second surface (7b) stably engaged to an annular zone of said adhesive surface (9a) surrounding the reference electrode (5);
   wherein said reference electrode (5) comprises an active portion (12) arranged in correspondence to said adhesive surface (9a) and a connecting portion (13) disposed in correspondence to said outer surface (9b); said active portion (12) having a surface coating (14) to promote the contact with the user's epidermis and to allow the electrical connection between the electrodes (3, 5);
   wherein the device further comprises a support base (18) of said electronic processor (16) and of said transducer (15), having an electrical connecting element (19) to said reference electrode (5) removably engaged to said connecting portion (13) of the reference electrode (5) to define a mechanical coupling between the reference electrode (5) coupled to the support element (9), and said support base (18); the connecting portion (13) of the reference electrode (5) comprising a protrusion (13a) insertable by mechanical interlocking within a seat (19a) formed in said connecting element (19) to define a mechanical coupling and electrical contact condition; said protrusion (13a) being extractable from the seat (19a) formed in the connecting element (19) to define a mechanical release condition with said base (18) and electrical disconnection with said transducer (15) and processor (16).

* * * * *